Figure 1:
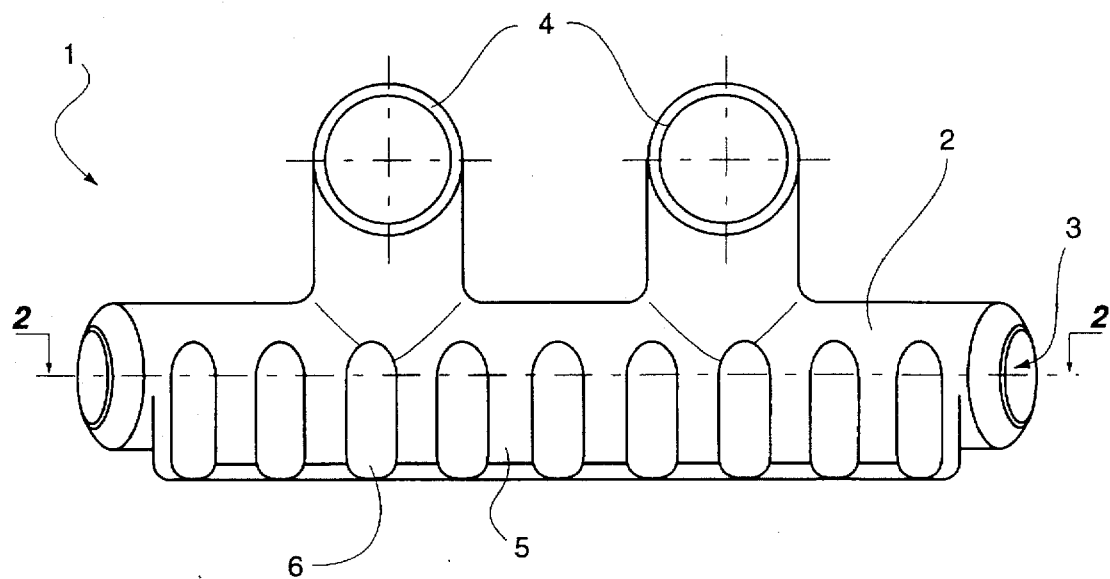

United States Patent [19]
Nielsen

[11] Patent Number: 5,740,799
[45] Date of Patent: Apr. 21, 1998

[54] DEVICE FOR THE SUPPLY OF OXYGEN AND/OR OTHER GASES TO A PATIENT

[75] Inventor: Lars Priess Nielsen, Hundested, Denmark

[73] Assignee: Maersk Medical A/S, Lynage, Denmark

[21] Appl. No.: 669,466

[22] PCT Filed: Dec. 21, 1994

[86] PCT No.: PCT/DK94/00482

§ 371 Date: Jun. 18, 1996

§ 102(e) Date: Jun. 18, 1996

[87] PCT Pub. No.: WO95/17220

PCT Pub. Date: Jun. 29, 1995

[30] Foreign Application Priority Data

Dec. 21, 1993 [DK] Denmark .................................. 1428/3

[51] Int. Cl.$^6$ .................................................. A61M 15/08
[52] U.S. Cl. ................................................ 128/207.18

[58] Field of Search ..................... 128/207.18, 207.12, 128/206.18, 206.21, 206.28

[56] References Cited

U.S. PATENT DOCUMENTS 3,682,171  8/1972  Dali et al. ..................... 128/207.18

*Primary Examiner*—Vincent Millin
*Assistant Examiner*—Robert N. Wieland
*Attorney, Agent, or Firm*—Thomas R. Vigil

[57] ABSTRACT

A device for the supply of oxygen and/or other gases to a patient comprises a flow conduit which is, at its one end, provided with means for fitting with e.g. an oxygen supply and, at its other end, closed, and having between its two ends a patient connection member (1) comprising upstream and downstream tubular members for insertion into a patient's nostrils and wherein the patient connecting member is provided with means (7) to increase the flow resistance beyond the first tubular member so as to create substantially even outflow amounts through the two respective tubular members.

9 Claims, 4 Drawing Sheets

DEVICE FOR THE SUPPLY OF OXYGEN AND/OR OTHER GASES TO A PATIENT

The present invention relates to a device for the supply of oxygen and/or other gases to a patient and comprising a flow duct which is, at its one end, provided with means for coupling to a supply source for oxygen and/or other gases and, at its other end, closed, and having between its two ends a patient connecting member comprising an upstream and a downstream tubular member, each of which is designed for insertion into the nostrils of a patient.

As used herein, the upstream tubular member is the tubular member which is most proximate to the gas supply relative to the flow duct. It is also referred to as the supply side.

Such device may for instance be used for the supply of gas in the form of oxygen to a bedridden patient through his nostrils. However, the gas supplied may also be a mixture of oxygen and for instance atmospheric air. For the sake of simplicity, however, the device will be referred to in the following as an oxygen supply device.

In the known oxygen supply devices of the type described above, however, such oxygen supply is effected in an inconvenient manner, especially when high flow rates are involved. It has been found that when supplied through the oxygen supply device, the oxygen flow in an amount suitable for the patient exits primarily through the downstream tubular member which has been inserted into the patient's one nostril. In some instances, the gas flow in the flow duct may even draw air out of the patient through the upstream tubular member. Of course, this results in considerably increased flow rates in the downstream tubular member, and as the gas flows into the patient's nose the nasal tissue will be exposed to correspondingly increased pressures which causes the patient much discomfort and in case of longterm insertion of the oxygen supply device, it may even be painful. Moreover, the increased flow rates for the oxygen causes the nasal mucosa to dry out thereby causing an irritation condition which is also very uncomfortable to the patient.

Thus, it is the object of the present invention to provide an oxygen supply device of the above-mentioned type which eliminates or attenuates the above drawbacks.

This is obtained with an oxygen supply device of the kind described above which is characterized in that the connecting member is constructed with means to increase the flow resistance beyond the upstream one of the tubular members to be inserted into the patient's nostrils.

Such oxygen supply device provides substantially even flow rates through the respective tubular members which are inserted into the patient's nostrils thereby reducing the patient's discomforts.

According to a convenient embodiment of the invention the means for increasing the flow resistance causes the flow area to be reduced beyond the upstream tubular member.

This reduction of the flow area may e.g. be established by increasing the wall thickness inwards in the flow duct in a section between the two tubular members, or the downstream tubular member may alternatively be constructed with a smaller flow area compared to the upstream tubular member.

The patient connecting member of the oxygen supply device is conveniently constructed as a separate element wherein at least the one end of the connecting member may be fitted with a first tubular connecting member which constitutes the flow conduit between the gas supply and the patient connecting member. The patient connecting member may be closed immediately at the downstream end so as to form the other, closed end of the flow conduit.

However, a flexible extension member, e.g. in the form of a second tubular conduit closed at one end, may advantageously be mounted at the downstream end of the patient connecting member, which extension member may be connected to the first tubular conduit member by means of a coupling device and thus it can serve to secure the oxygen supply device behind the patient's head.

Figure 2:
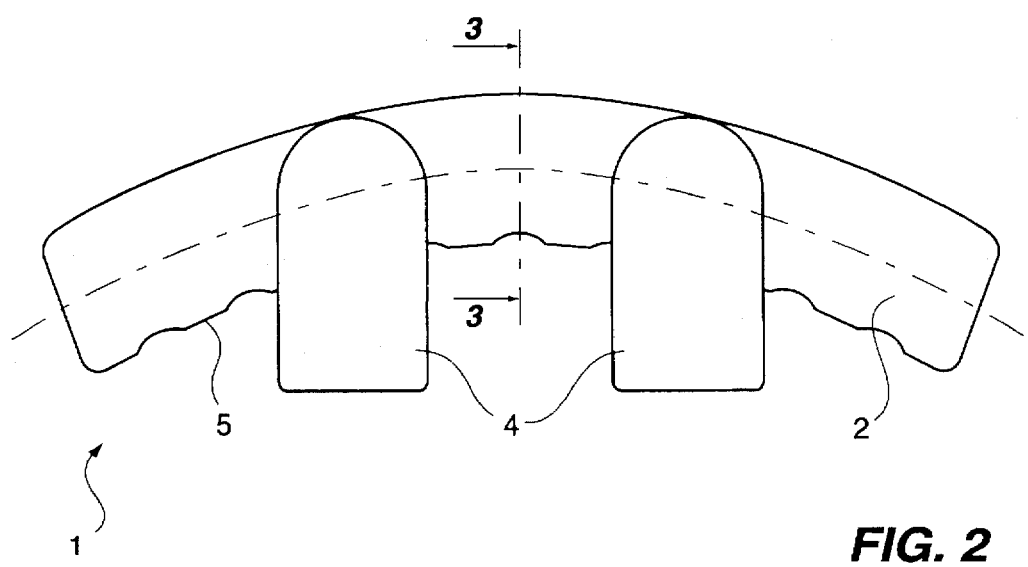
Figure 3:
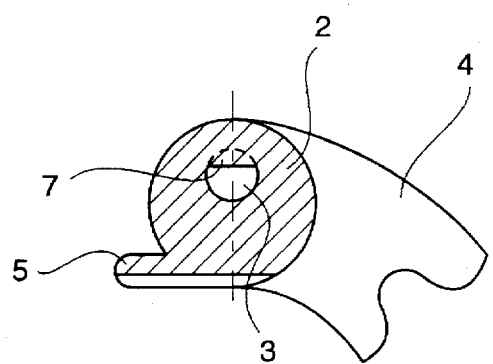
Figure 4:
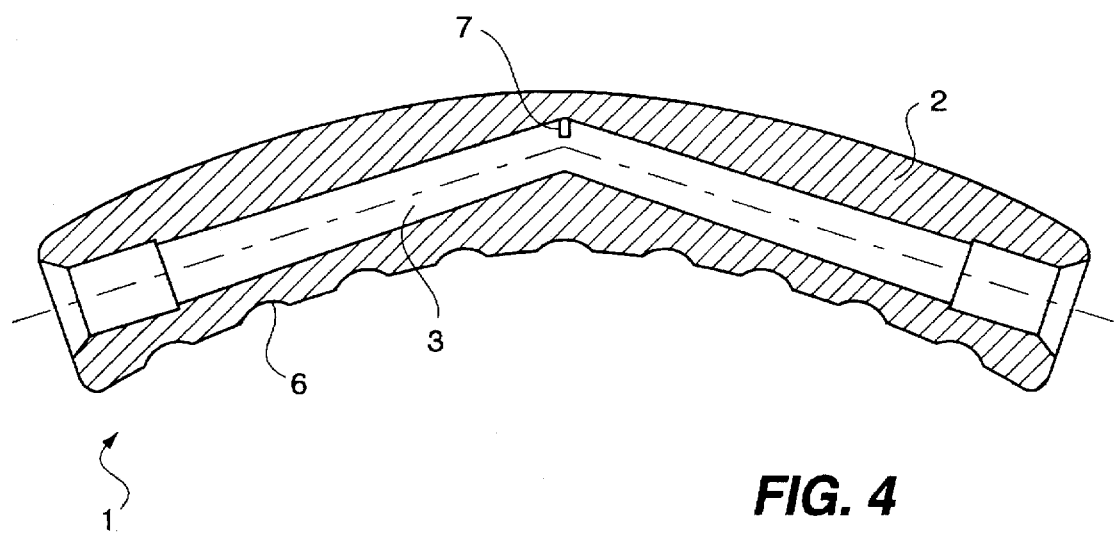
Figure 5:
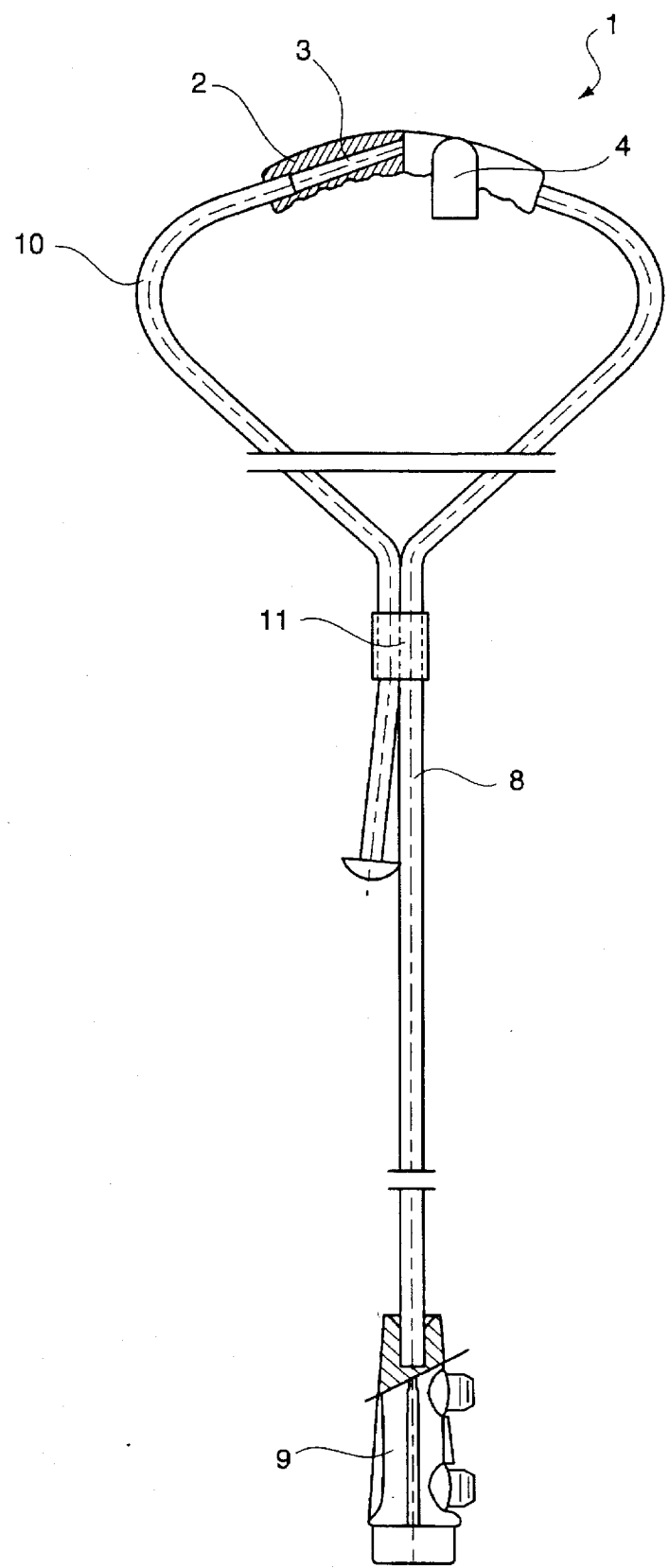

In the following the invention will be described in further detail with reference to the drawings, wherein FIG. 1 is a patient's view of an embodiment of a connecting member, FIG. 2 is a top plan view of a connecting member corresponding to the one shown in FIG. 1, FIG. 3 is a sectional view through a connecting member along the line B—B in FIG. 2, FIG. 4 is a sectional view of a connecting member according to the line A—A in FIG. 1, FIG. 5 shows a device according to the invention utilizing a patient connecting member as shown in FIGS. 1–4, FIG. 6 is a flow chart outlining the flow conditions following varying area reductions, wherein the area reduction is shown as a percentage of the total clearance, and As will appear from FIGS. 1 and 2 the patient connecting member 1 of a device according to the invention comprises a flow conduit 2 from where two tubular members 4 extend which are intended for insertion into the patient's nostrils and are in flow communication with the flow path 3 of the flow conduit 2. In the embodiment shown, the connecting member 1 is open in both ends of the flow conduit 2.

The tubular member which is most proximate to the oxygen supply is referred to as the upstream tubular member whereas the tubular member which is most proximate to the closed end of the device is referred to as the downstream tubular member.

Moreover, the flow conduit 2 comprises a tangent surface 5 which faces the patient in its fitted state and is provided with a number of recesses 6 which, in the fitted state where the surface rests against the patient's upper lip, permit air to enter through the connecting member and the upper lip thereby reducing the discomforts which result from the insertion of the oxygen supply device. However, this is not essential to the invention.

It will appear from FIG. 3 that the wall thickness of the flow conduit in a section 7 has been increased inwards in the flow duct to reduce the flow area. This will also appear from FIG. 4. In the embodiment shown, the cross section which in the remaining portion of the flow duct is circular, is cut off, the wall material thus forming a chord through the circular cross section, hereby establishing increased flow resistance.

By the establishment of increased flow resistance beyond the first tubular member, the flow rate on the relevant site is throttled and this results in substatially uniform static pressures at the outlet openings of the two tubular members which ensures that essentially even amounts of oxygen flow out through the respective outlet openings of the two tubular members.

FIG. 5 shows a device according to the invention. To the one end of the patient connecting member 1, a tubular conduit 8 is fitted which, via a coupling element 9, is at its opposite end connectable to an oxygen source (not shown), e.g. a pressure gas cylinder. In the embodiment shown, the patient connecting member is designed symmetrically and thus it will be possible to connect the tubular conduit 8 to any of the two ends of the patient connecting member. Thus, the definition of the upstream and the downstream tubular member will depend on which side is chosen for the fitting of the tubular conduit 8. In instances where one of the tubular members 4 has a reduced flow cross section compared to the other or where for instance the flow path 3 has a smaller inner diameter in an area extending from an area between the two tubular members and beyond the one tubular member, the desired result may only be obtained by connecting the tubular member to that end of the patient connecting member which is most proximate to the tubular member with the largest flow cross section, or alternatively, to that end from which the tubular member extends from the flow path with the largest diameter.

Figure 6:
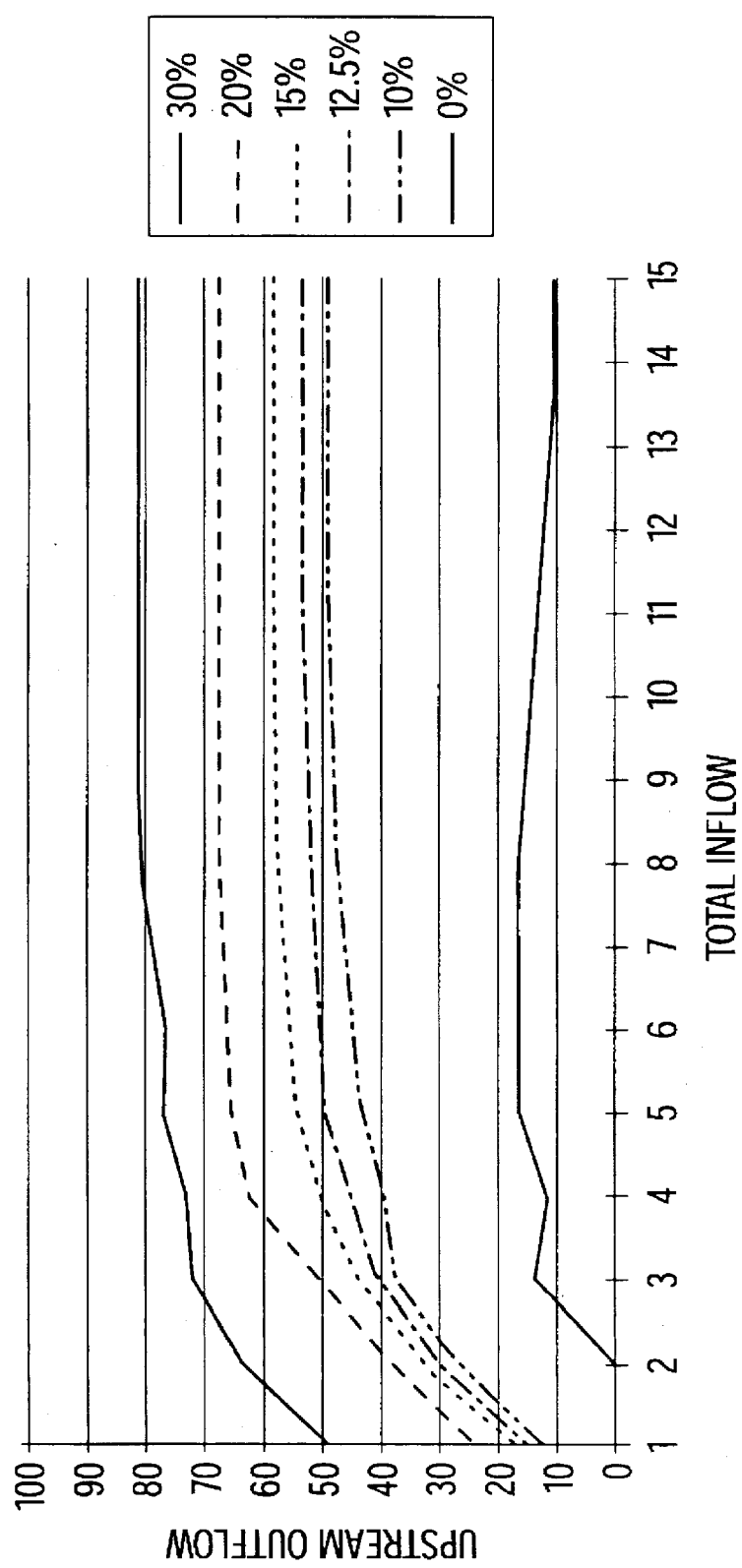

In a series of tests with oxygen supply devices of the type described herein the measurement results shown in FIG. 6 were obtained. They indicate the outflow amounts from the two tubular members relative to the oxygen amount supplied at different values for the oxygen amount supplied. The axis of abscissae indicates the total outflow of oxygen and the axis of ordinates indicates the oxygen amount which flows out through the upstream tubular member which is most proximate to the oxygen supply.

It will appear from the lowermost curve that with the selected clearance in the flow duct and without means for increasing the flow resistance, outflow of the major part (80–90%) of the oxygen through the downstream tubular member occurs which, of course, leads to considerably increased flow rates at this point and evidently the above-mentioned drawbacks will arise. It will also appear that with a reduction of the clearance in the flow duct between the two tubular members of 10%, 12,5% and 15% the oxygen outflow is substantially the same for the two tubular members. In case of a 20% and 30% reduction of the clearance, the outflow through the upstream tubular member begins to exceed the outflow through the downstream tubular member. However, other dimensions of the total clearance of the flow duct may require a larger area reduction than the optimum reduction given in the chart, viz. of 10–15%, to obtain the desired effect of the invention.

The oxygen supply device described herein serves exclusively as an example and several variations of the embodiment will thus be possible without departing from the scope of the appended patent claims.

I claim:

1. A device for the supply of oxygen and/or other gases to a patient and comprising a flow conduit which is, at its one end, provided with means for coupling to a supply source for oxygen and/or other gases and, at its other end, closed, and having between its two ends a patient connecting member comprising an upstream and a downstream tubular member each of which is designed for insertion into the nostrils of a patent, wherein, in the patient connecting member beyond the upstream one of the tubular members for insertion into the patient's nostrils, flow restriction means are provided for equalizing the outflow through the upstream and the downstream tubular member.

2. A device according to claim 1, wherein the patient connecting member is provided as a separate element having end sections adapted to be fitted with a tubular conduit on at least its one side.

3. A device according to claim 1 wherein the downstream end of the patient connecting member is fitted with a flexible extension member for securing the oxygen supply device behind the patient's head by means of a coupling device which connects the extension member and the tubular conduit.

4. A device according to claim 1, wherein the flow restriction means is provided by the fact that the downstream tubular member for insertion into a patient's nostrils has a flow area which is smaller than the flow area of the upstream tubular member.

5. A device according to claim 1, wherein the flow restriction means is provided by reducing the flow area by increasing the wall thickness of the connecting member inwards in the flow conduit in a section between the tubular members to be inserted into the patient's nostrils.

6. A device according to claim 2, wherein the area reduction beyond the upstream tubular member amounts to between 5 and 25%.

7. A device according to claim 2 wherein the area reduction beyond the upstream tubular member amounts to between 10 and 20%.

8. A device according to claim 3, wherein the area reduction beyond the upstream tubular member amounts to between 5 and 25%.

9. A device according to claim 2 wherein the area reduction beyond the upstream tubular member amounts to between 10 and 20%.

* * * * *